United States Patent
Peters

(10) Patent No.: US 6,512,439 B1
(45) Date of Patent: Jan. 28, 2003

(54) COIL

(76) Inventor: Olaf Peters, Holztratten 17, Dellach/Drau (AT), A-9772

( * ) Notice: Subject to any disclaimer, the term of this patent is extended or adjusted under 35 U.S.C. 154(b) by 0 days.

(21) Appl. No.: 09/868,144

(22) PCT Filed: Nov. 2, 2000

(86) PCT No.: PCT/EP00/10781
§ 371 (c)(1),
(2), (4) Date: Jun. 15, 2001

(87) PCT Pub. No.: WO01/35425
PCT Pub. Date: May 17, 2001

(30) Foreign Application Priority Data

Nov. 11, 1999 (DE) .......................... 199 54 367
Feb. 10, 2000 (DE) .......................... 100 05 917

(51) Int. Cl.⁷ .............................................. H01F 27/28
(52) U.S. Cl. ........................ 336/180; 336/233; 336/192
(58) Field of Search ........................ 336/83, 180, 233, 336/192, 200; 310/71; 29/606, 596

(56) References Cited

U.S. PATENT DOCUMENTS

| | | | | |
|---|---|---|---|---|
| 5,554,181 A | * | 9/1996 | Das | 623/1 |
| 5,906,639 A | * | 5/1999 | Rudnick et al. | 623/1 |
| 5,931,830 A | * | 8/1999 | Jacobsent et al. | 604/523 |
| 6,239,681 B1 | * | 5/2001 | Buswell | 336/83 |

FOREIGN PATENT DOCUMENTS

| | | | |
|---|---|---|---|
| DE | 24 05 383.6 | 2/1974 | H01F/5/02 |
| DE | 195 43 573.7 | 11/1995 | H01F/5/00 |
| DE | 296 08 779.3 | 5/1996 | H01F/5/00 |
| GB | 1275859 | 11/1970 | B65H/81/06 |
| JP | 63233224 | 9/1988 | H01F/5/00 |

OTHER PUBLICATIONS

Seike, S., "The Principals of Ultra Relativity," *Space Research Institute*, 12th Edition, Apr. 15, 1994.

* cited by examiner

Primary Examiner—Anh Mai
(74) Attorney, Agent, or Firm—Brinks Hofer Gilson & Lione

(57) ABSTRACT

The presented invention concerns a coil formed by windings of a first electrical wire and windings of at least one more electrical wire whereby the wires are connected with each other at their respective ends.

The starting points of the individual windings of the first electrical wire and of at least one more electrical wire are shifted against each other along the circumference of the coil body. Each wire forms a redirection point after approximately one loop at which it traverses under itself and then crosses over the neighboring wire windings along the axis of the coil until it is redirected to run parallel to the other wire layers around the coil body. Thus, the windings of different wires alternate in a predetermined manner along the coil axis.

19 Claims, 3 Drawing Sheets

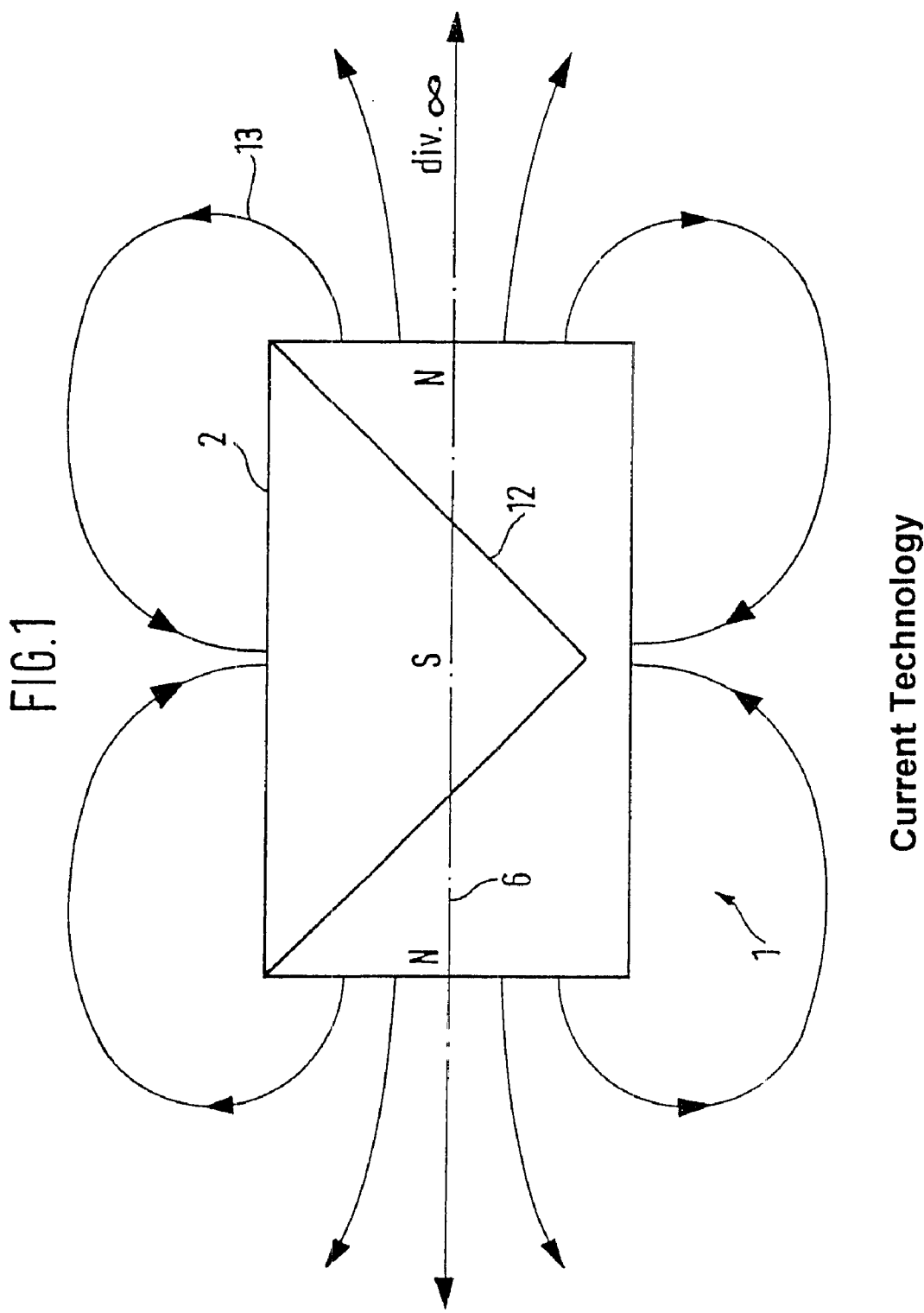

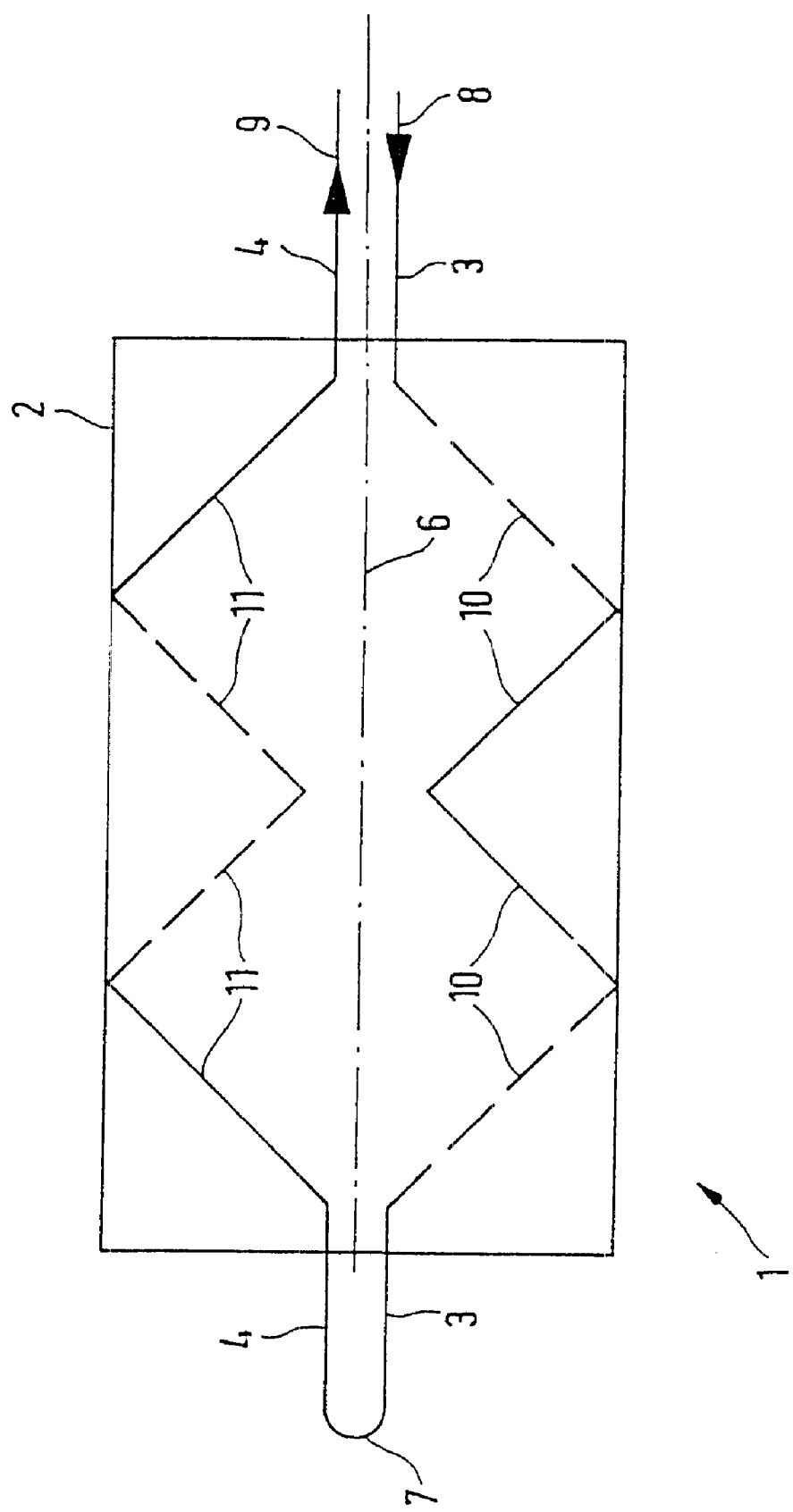

COIL

BACKGROUND OF THE INVENTION

The invention described herein concerns a coil that can be used for generating scalar fields.

The Klein winding technique or the Möbius coil (August Ferdinand Möbius, German mathematician and astronomer, Nov. 17, 1790 to Sep. 26, 1868) is well known from technical applications (Sinichi SEIKE in "The Principles of Ultrarelativity", Space Research Institute, Ninomiya Press 1994).

This coil form was developed because the magnetic field of this kind of winding, if generated by DC currents, produces a field that is equivalent to the topology of a Klein bottle (Felix Klein, German mathematician, Apr. 25, 1849 to Jun. 22, 1925). One coil, spooled half on the left and half on the right, functions as a magnetic quasi-single pole with a field force distribution in which two equal poles are located at the ends and a counter pole in the middle of the coil. One-sixth of each end field forms closed field lines with one-third of the center pole. One-sixth of the field at each end of the coil shows infinite divergence (div $\infty$) and behaves like an electrical field line. This behavior results in an array of phenomena which are equally important to space physics and biology.

This kind of winding is achieved when the individual loops are placed around the coil core in "half hitch".

Such a Möbius coil is shown in FIG. 1 in which a coil 1 has a coil body 2 around which the individual windings of an electrical wire are spooled, as in a regular coil. Diverging from regular technical methods, however, the individual windings are spooled around the coil body 2 in "half hitch" resulting in a V-shaped knot line 12.

This kind of spooling does not allow creation of a bifilar winding.

The task of the presented invention is to provide a coil for generating scalar fields.

SUMMARY OF THE INVENTION

This task can be accomplished by a coil with a coil body having an axis, and windings of a first electrical wire and windings of at least one more electrical wire around the coil body. Each of the wires have a first and a second end and a loop connecting the second end of the first wire to the first end of a first of the at least one more electrical wire. Electrical connections connected at the first end of the first wire and at the second end of a last of the at least one more electrical wires. The individual windings of the first wire and the windings of the at least one more wire begin at starting points which are shifted against each other along the circumference of the coil body. Further, each wire crosses under itself after about one rotation at a redirection point and each wire crosses over a next adjacent winding along the axis of the coil before being wrapped around the coil body again, so that the windings of different wires alternate along the axis of the coil body.

The cylindrical coil according to this invention (multiple Kleinean roll) contains windings of a first electrical wire and another wire, e.g., as a second electrical conductor. The wires are connected with each other at their respective ends as functionally appropriate. In the case of a bifilar Kleinean roll containing a first and second wire, the wires are connected electrically with each other at one end of the coil so that each wire can serve for flow in opposite directions. The coil is spooled in such a way that the individual windings of the individual electrical wires are shifted against each other along the circumference of the coil body. If two wires are used, it is advantageous to offset them by 180 degrees so that the windings of both electrical wires begin on opposite sides of the coil body.

After approximately one full loop, each of the wires is redirected so that each wire traverses underneath itself and then crosses over the neighboring wire windings along the axis of the coil, until it is redirected again to run parallel to the other wire layers around the coil body. Thus, the windings of the first electrical wire and the additional electrical wire alternate along the coil axis. The redirection points (knots) resulting from this kind of arrangement can be placed along the axis of the coil in a straight line or in a zigzag line, e.g., like a series of V's. It offers certain advantages to create a V-shaped knot line in which the direction of the electrical wires changes at each tip of the V, thereby reversing right-looping windings into left-looping windings and vice versa.

In other words, in a coil with two wires with diametrically opposed starting points, which is constructed according to the invention, each wire is placed in alternating "half hitch". At the end of the coil the wire ends are connected with each other so that the current in two neighboring windings flows in opposite directions. The magnetic fields will thus cancel each other out. In a vector diagram, the magnetic field vector argument becomes irrelevant, i.e., it is exactly zero since, according to the $2^{nd}$ Kirchhoff Law, a current is equal in size to its counter current.

Fields, in which the arguments of the field vectors are zero, are called scalar fields. Their presence in the coil constructed according to the invention is assured since the energy conservation law stipulates that the applied electrical energy cannot disappear (K. Meyl, "Elektromagnetische Unverträglichkeit, Ursachen, Phänomene und naturwissenschaftliche Konsequenzen. Umdruck zur Vorlesung" [Electromagnetic Incompatibility, Causes, Phenomena and Scientific Consequences, Reprint for the Lecture], ISBN 3-9802-6428-3 and ISBN 3-9802-542-9-1, and K. Meyl, "Potentialwirbel [Potential Vortex], Vol. 1 and 2, ISBN 39802-542-1-6 and ISBN 3-9802-542-2-4).

The following are a few examples of coils constructed according to the invention.

BRIEF DESCRIPTION OF THE DRAWINGS

FIG. 1 shows a regular Möbius coil;

FIG. 2 shows a coil according to the invention; and

DESCRIPTION OF THE PREFERRED EMBODIMENTS

Figure 3A:
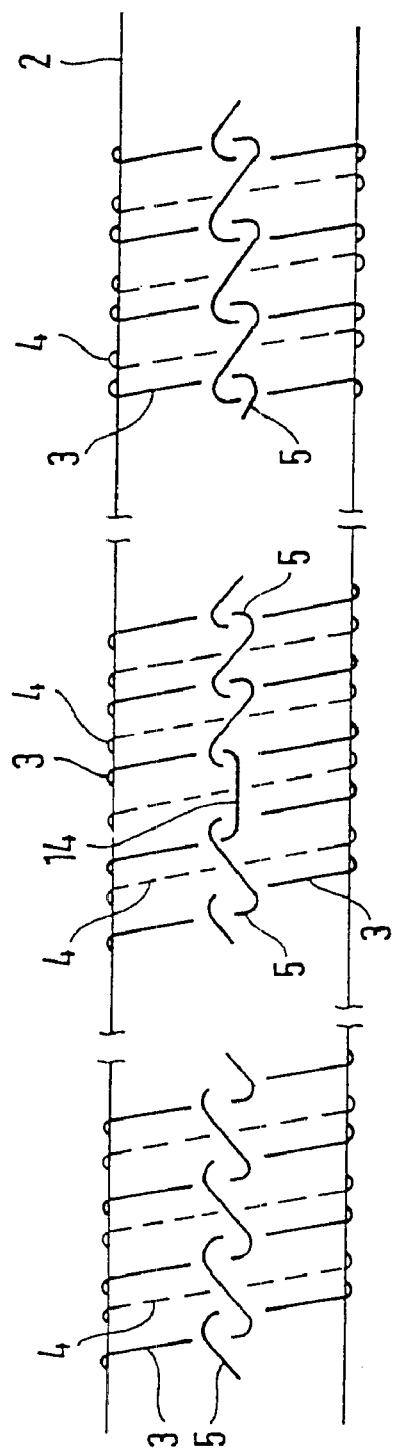
FIG. 3 shows two different kinds of windings on a coil according to the invention.

FIG. 2 shows a coil 1 with a coil body 2 onto which two electrical wires 3 and 4 are spooled. The wires 3 and 4 are wrapped according to the method described above so that one wire 3 always loops around the core parallel to the neighboring wire 4. The knots of the wire 3 form the V-shaped knot line 10. It should be noted that the solid lines in the figure show the top view as seen by an observer whereas the broken lines depict how the knot line 10 continues on the rearside of the coil body 2. This also applies to the knot line 11 of the wire 4, which is shifted by 180 degrees along the circumference of the coil body. The wires 3 and 4 are connected separately at 8 and 9, respectively, and are electrically linked at the reversal loop 7 at the other end of the coil.

FIG. 3 shows each knot formation according to the invention in the partial illustrations A and B. FIG. 3A displays a knot line which runs along the axis of the coil body 2 in a straight line.

The wire 3 is looped around the coil body 2, then pulled through underneath itself and placed again above itself and above the neighboring second wire 4 before it is wrapped around the coil body 2 again in a new loop. The same procedure in a symmetrical pattern is used for the wire 4, resulting in the knots (redirection points) 5. The redirection points 5 are placed next to each other in a straight line along the axis of the coil body 2. The center of FIG. 3A shows how the wire 3 is placed to form a point of direction change. This means that the wire 3, which was looped to the right up to this point, is looped to the left after the reversal point the knots 5 following after this reversal point 14 are created in the previously described way.

The second wire 4 is represented in FIG. 3 as a broken line. A similar knot line, which is not depicted in the illustration, is created for this wire on the backside of the coil body 2.

If a linear knot line is created the coil will act as a magnetic dipole under an electrical current.

Figure 3B:
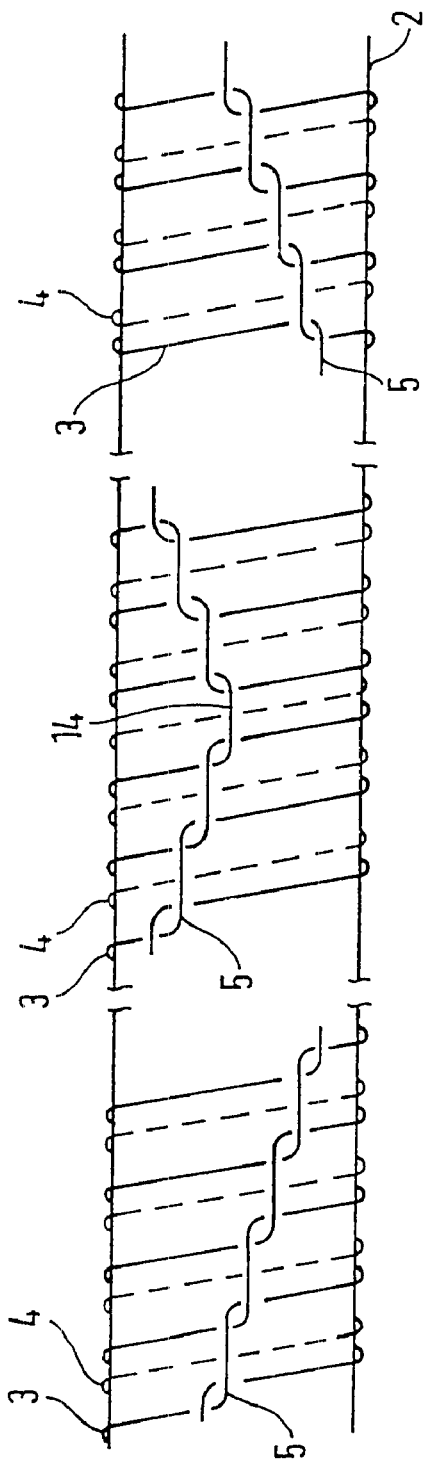

FIG. 3 also shows how the knots can be placed in a V-shape. Each knot is shifted slightly against the neighboring knot along the circumference of the coil body 2. The center of FIG. 3B illustrates how creating a directional reversal point 14 forms the typical V-shape. The directional reversal point 14 is at the tip of the V.

If the coil according to the invention is built as shown in FIG. 3B with reversal points 5 in a V-shape, the coil will act as a magnetic tripole under an electrical current.

What is claimed is:

1. A coil comprising a coil body having an axis, and windings of a first electrical wire and windings of at least one more electrical wire around the coil body, each of the wires having a first and a second end, a loop connecting the second end of the first wire to the first end of a first of said at least one more electrical wire, electrical connections connected at the first end of the first wire and at the second end of a last of said at least one more electrical wire, wherein the individual windings of the first wire and the windings of the at least one more wire begin at starting points which are shifted against each other along the circumference of the coil body, and wherein each wire crosses under itself after about one rotation at a redirection point and each wire crosses over a next adjacent winding along the axis of the coil before being wrapped around the coil body again, so that the windings of different wires alternate along the axis of the coil body.

2. A coil according to claim 1 wherein said at least one more electrical wire comprises a second electrical wire as an additional electrical conductor wrapped around the coil body and wherein the first and the second electrical wires are electrically connected with each other at one end of the coil.

3. A coil according to claim 1 or 2 wherein the direction of the winding of at least one electrical wire is reversed at least once along the axis of the coil.

4. A coil according to claim 3 wherein the direction of the winding is reversed at a redirection point.

5. A coil according to claim 1 wherein the redirection points of the first electrical wire are shifted around the circumference of the coil by approximately 180 degrees against said at least one more electrical wire.

6. A coil according to claim 1 or 5 wherein the redirection points of one of the first wire and said at least one more wire form a straight line parallel to the axis of the coil.

7. A coil according to claim 1 or 5 wherein the redirection points of one of the first wire and said at least one more wire form a zigzag line along the coil.

8. A coil according to claim 7 wherein the redirection points of one of the first wire and said at least one more wire are placed along the coil in a V-shape.

9. A coil according to claim 7 wherein the direction of the windings of the wire is reversed at the points at which the zigzag line formed by the redirection points intersect in an angle.

10. A coil according to claim 1 or 5 wherein the coil body has a cylindrical shape.

11. A coil comprising a coil body having an axis, a first wire and a second wire, each of the first and second wires including a plurality of half hitch loops arranged around the coil body, adjacent pairs of the half hitch loops of the first wire being interspaced by a half hitch loop of the second wire, a linear segment of the first wire joining each adjacent pair of half hitch loops of the first wire and a linear segment of the second wire joining each adjacent pair of half hitch loops of the second wire, each linear segment in the first wire crossing one of the loops of the second wire and each linear segment in the second wire crossing one of the loops of first wire, each of the wires having a first and a second end, a reversal loop connecting the second end of the first wire to the first end of the second wire, and electrical connections connected at the first end of the first wire and at the second end of the second wire.

12. A coil according to claim 11 wherein the linear segments of the first and second wire are arranged parallel to said axis.

13. A coil according to claim 11 or 12 wherein the linear segments of the first and second wire include end points at which the linear segment integrally joins the half hitch loops.

14. A coil according to claim 13 wherein the end points are arranged parallel to said axis.

15. A coil according to claim 13 wherein the end points are arranged in a zigzag line along the coil body.

16. A coil according to claim 13 wherein the end points are arranged in a V-shape along the coil body.

17. A coil according to claim 13 wherein the coil body is cylindrical.

18. A coil according to claim 17 wherein the end points of the first electrical wire are shifted around the coil body by approximately 180 degrees with respect to the end points of the second electrical wire.

19. A coil according to claim 13 wherein the direction of the loops of at least one of the first and second wires is reversed at least once along the axis of the coil.

* * * * *